United States Patent [19]

Mittleman et al.

[11] Patent Number: 6,078,047

[45] Date of Patent: Jun. 20, 2000

[54] METHOD AND APPARATUS FOR TERAHERTZ TOMOGRAPHIC IMAGING

[75] Inventors: Daniel Matthew Mittleman, Houston, Tex.; Martin C. Nuss, Fair Haven, N.J.

[73] Assignee: Lucent Technologies Inc., Murray Hill, N.J.

[21] Appl. No.: 08/877,054

[22] Filed: Jun. 17, 1997

Related U.S. Application Data

[60] Provisional application No. 60/040,452, Mar. 14, 1997.

[51] Int. Cl.[7] .......................... G01N 21/17; G01N 21/49
[52] U.S. Cl. ........................ 250/338.1; 250/330
[58] Field of Search .................. 250/338.1, 330, 250/341.1

[56] References Cited

U.S. PATENT DOCUMENTS

| | | | |
|---|---|---|---|
| 5,623,145 | 4/1997 | Nuss | 250/330 |
| 5,710,430 | 1/1998 | Nuss | 250/358.1 |
| 5,789,750 | 8/1998 | Nuss | 250/338.1 |
| 5,894,125 | 4/1999 | Brener et al. | 250/330 |
| 5,939,721 | 7/1999 | Jacobsen | 250/330 |

OTHER PUBLICATIONS

A. C. Kak, et al., "Principles of Computerized Tomographic Imaging," p. 298 ff., IEEE Press, New York (1988).

Mittleman, D. M. et al., "T–Ray Imaging", IEEE Journal On Selected Topics In Quantum Electronics, Sep. 1996, IEEE, USA, vol. 2, No. 3, pp. 679–692.

Mittleman, D. M. et al., "T–Ray Tomography" Optics Letters, Jun. 15, 1997, OPT. SOC. America, USA, vol. 22, No. 12, pp. 904–906.

Primary Examiner—Edward P. Westin
Assistant Examiner—Richard Hanig
Attorney, Agent, or Firm—J. J. Brosemer

[57] ABSTRACT

Providing a compositional image of an object in real time is accomplished by illuminating the object with a waveform comprising pulses of electromagnetic radiation in the terahertz frequency range and measuring the relative time delays of pulses reflected by the object to determine the positions of dielectric interfaces in the object. According to a further embodiment, the waveform includes one or more pulses of terahertz radiation, each pulse having a duration in the range of approximately 10 to 10,000 femtoseconds.

27 Claims, 3 Drawing Sheets

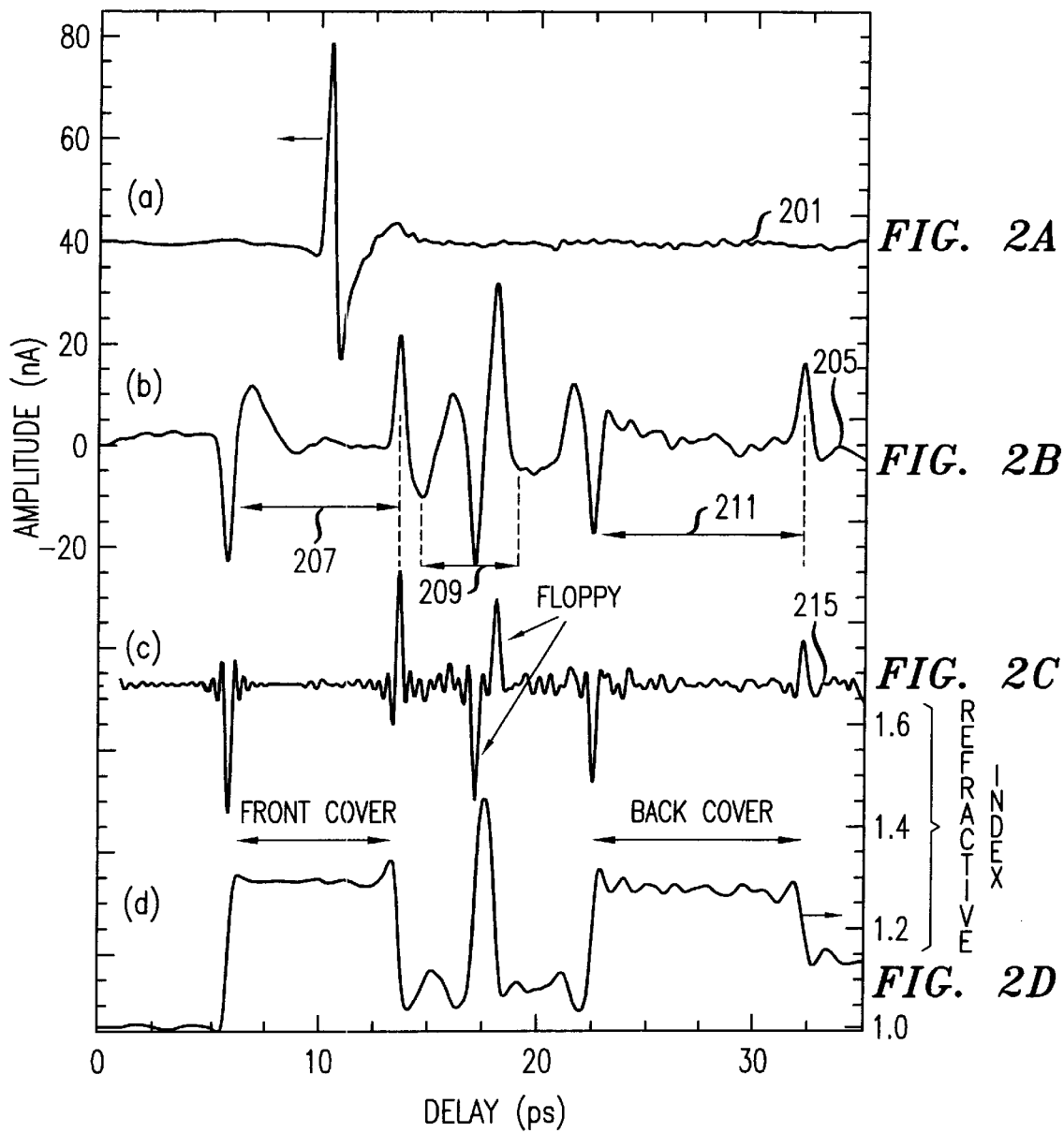

METHOD AND APPARATUS FOR TERAHERTZ TOMOGRAPHIC IMAGING

CROSS-REFERENCE TO RELATED APPLICATION

This application claims priority of Provisional Application Ser. No. 60/040,452 which was filed Mar. 14, 1997.

BACKGROUND OF THE INVENTION

1. Field of the Invention

The invention relates generally to electromagnetic imaging, and more particularly to imaging techniques that operate in the terahertz frequency range.

2. Background Art

Time-domain measurements of electromagnetic radiation in the terahertz frequency range have been used in the operational environment of spectroscopy. However, the use of terahertz electromagnetic radiation to provide an image of an object in real time is impractical due to the relatively long acquisition time required for terahertz waveforms. This acquisition time is typically in the range of minutes. Using pulses of terahertz radiation, one presently-existing terahertz ("T-ray") imaging technique reduces the acquisition time of a single terahertz waveform from several minutes to several milliseconds, while still maintaining a reasonable signal-to-noise ratio. Examples of this technique are disclosed in U.S. Pat. No. 5,623,145 issued Apr. 22, 1997, to Martin C. Nuss and also in patent application Ser. No. 08/711,146, filed Sept. 9, 1996, M. C. Nuss now U.S. Pat. No. 5,789,750. However, this technique does not explicitly utilize the time-domain nature of the terahertz waveform. Consequently, the displayed images only show the transmitted or reflected power, obtained by integrating the Fourier spectrum of the terahertz waveform with a digital signal processor (DSP). Such an image is not a full-volume image, which is defined as an image that shows the locations of compositional discontinuities within the volume of an object. Images that only show transmitted and/or reflected power do not reveal compositional information about an object including the locations of discontinuities. What is needed is an improved terahertz imaging technique which provides depth resolution and compositional information about an object in real time.

SUMMARY OF THE INVENTION

Providing a depth-resolved compositional image of an object in real time is accomplished by illuminating the object with a waveform comprising pulses of electromagnetic radiation in the terahertz frequency range and measuring the relative time delays of pulses reflected by the object to determine the positions of discontinuities in the object. According to a further embodiment, the waveform includes one or more pulses of terahertz radiation, each pulse having a duration in the range of approximately 10 to 10,000 femtoseconds.

BRIEF DESCRIPTION OF THE DRAWINGS

FIGS. 2A, 2B, 2C, and 2D are graphs of, respectively, a terahertz waveform used to illuminate a test object; a terahertz waveform reflected by the test object; a waveform reflected by the test object to which signal processing techniques have been applied; and a curve from which a refractive index profile is retrieved.

DETAILED DESCRIPTION OF THE PREFERRED EMBODIMENTS

Figure 1:
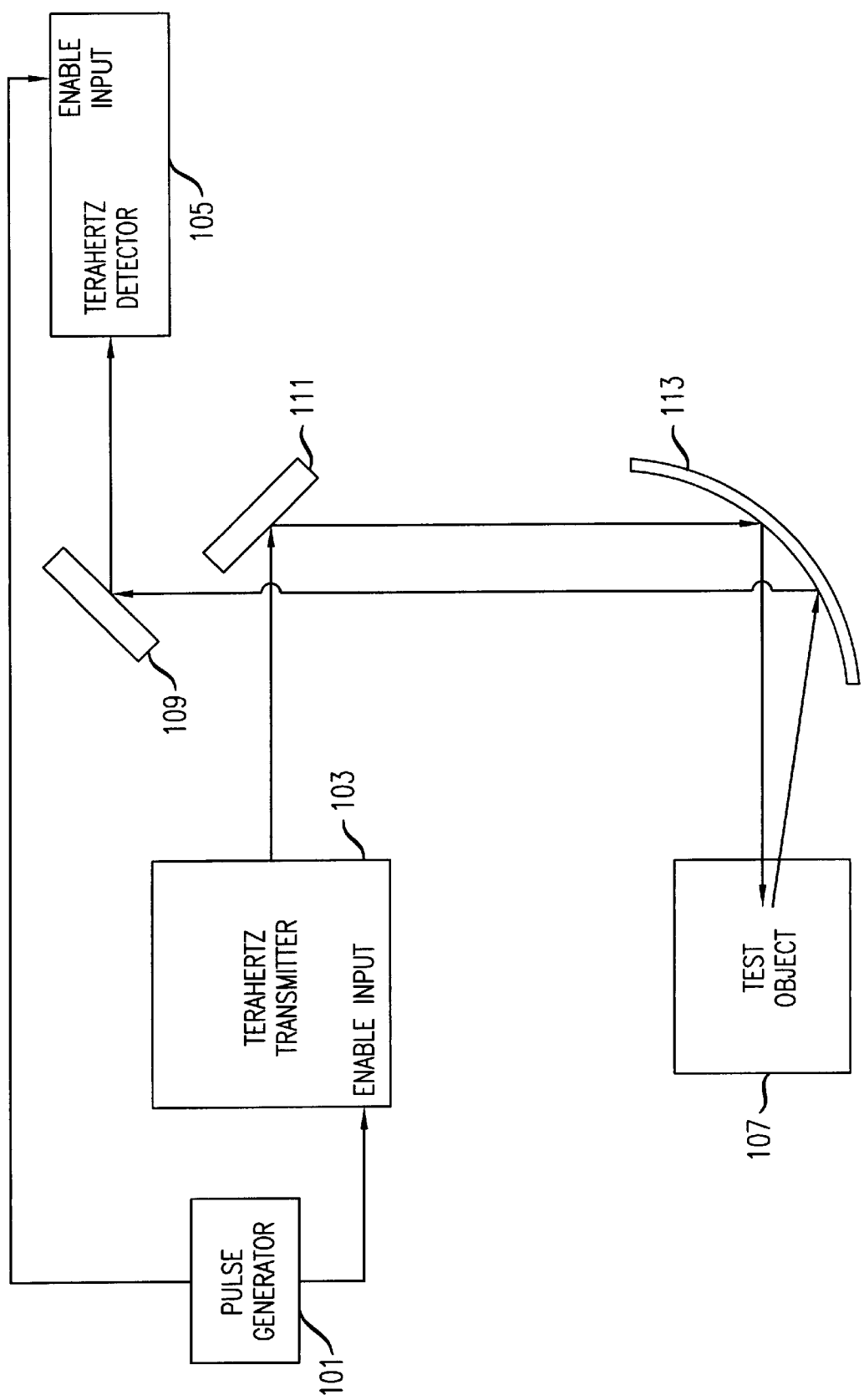
FIG. 1 is a hardware block diagram and partial pictorial representation of a terahertz imaging system constructed according to a preferred embodiment disclosed herein.

FIG. 1 is a hardware block diagram and partial pictorial representation of a terahertz imaging system constructed according to a preferred embodiment disclosed herein. A terahertz transmitter 103 provides a source of terahertz electromagnetic radiation. Terahertz transmitter 103 is controlled by means of an enable input. The state of the enable input is related to the output of the transmitter. For example, when a pulse is present at the enable input of transmitter 103, the transmitter is turned on, providing electromagnetic energy in the terahertz frequency range for a certain time duration which may, but need not, be substantially equal to the duration of the pulse. By way of an illustrative example, when a pulse is present at the enable input, this may result in activation of terahertz transmitter 103 for a specified period of time (unrelated to the pulse duration), after which the transmitter 103 automatically turns off. In the case where no pulses have been applied to the enable input of transmitter 103 for a specified period of time, the transmitter is turned off, and terahertz electromagnetic radiation is not generated.

The enable input of terahertz transmitter 103 is coupled to a pulse generator 101. Pulse generator 101 generates optical gating pulses that have a duration in the range of approximately 10 to 10,000 femtoseconds. In this manner, the pulse generator 101 controls terahertz transmitter 103 such that the transmitter generates bursts of terahertz electromagnetic radiation where each burst is in the range of about 10 to 10,000 femtoseconds. The electromagnetic radiation generated by transmitter 103 is in the form of a beam of terahertz pulses.

The beam of terahertz pulses generated by transmitter 103 is incident upon first reflective surface 111, which reflects substantially all of the beam to a second reflective surface 113. In the present example, the first reflective surface 111 is flat and the second reflective surface is parabolic. Substantially all of the beam reflected by the second reflective surface 113 is aimed at a test object 107. The second reflective surface 113 may be positioned such that the beam of terahertz pulses are incident upon the test object 107 at a nearly normal angle of incidence, and such that the beam comes to a focus at or near the surface of the test object 107. In an illustrative implementation of the system shown in FIG. 1, the beam is brought to a focus substantially at the surface of test object 107 by setting the confocal parameter of the second reflective surface 113 to an appropriate value related to the distance between the test object 107 and the second reflective surface 113. When the beam is brought to a focus at or near the surface of test object 107, this results in enhanced spatial resolution corresponding to diffraction-limited performance.

A portion of the beam of terahertz pulses that are incident upon test object 107 are reflected by the test object. This reflected beam of terahertz pulses is then re-collimated by the second surface 113, then captured by a third reflective surface 109, which directs the reflected beam to a terahertz detector 105. The beam is typically reflected by the test object 107 at a near-normal angle of incidence. For a test object 107 having multiple reflecting surfaces within, the waveform returned from the test object consists of a plurality of replicas of the waveform incident thereupon, with each reflecting surface returning a corresponding replica of the incident waveform. If the incident waveform is a single pulse of terahertz radiation, the waveform reflected from the test object includes a plurality of pulses of various magnitudes, polarities, and temporal distortions, reflected from dielectric discontinuities within the object.

Refer to FIGS. 2A–2D which were prepared using a conventional 3.5-inch floppy disk as test object 107 (FIG. 1), The beam of terahertz pulses is directed by reflective surfaces 111, 113 such that the beam is incident upon, and reflected from, substantially a single point on the floppy disk. FIG. 2A is a graph of a terahertz pulse which is incident upon the 3.5" floppy disk, FIG. 2B is a graph of a terahertz waveform reflected by the floppy disk, and FIG. 2C is a graph of the waveform of FIG. 2B to which signal processing techniques have been applied pursuant to a preferred embodiment disclosed herein. FIG. 2D is a graph of the index profile of the object, and is obtained from the waveform of FIG. 2C.

The waveform 201 of FIG. 2A may be measured at the output of terahertz detector 105 (FIG. 1) by replacing test object 107 (FIG. 1) with a mirror or other object that reflects substantially all terahertz radiation incident thereupon with little or no reflection loss. In such a case, waveform 201 represents an inverted-polarity replica of the terahertz pulse incident upon test object 107 (FIG. 1). Waveform 201 (FIG. 2A) is inverted in polarity from the actual waveform that is incident upon test object 107 (FIG. 1) due to the 180-degree phase shift that occurs at the aforementioned mirror or other metallic objects. The small oscillations which follow a main pulse 202 in waveform 201 are a result of residual water vapor in the beam path, and do not affect system operation in any significant manner.

Waveform 205 (FIG. 2B) is a representative waveform reflected by test object 107 (FIG. 1) as measured at terahertz detector 105. This waveform 205 (FIG. 2B) actually consists of a series of "distorted replicas" 207, 209, 211 of incident waveform 201. Each distorted replica 207, 209. 211 of incident waveform 201 corresponds to a particular reflection from a specific compositional discontinuity of the floppy disk. One type of compositional discontinuity is a dielectric interface. Such dielectric interfaces may occur where air meets plastic, where plastic meets air, or from the surfaces of the magnetic recording material. The polarity and magnitude of each reflection are determined by the reflection coefficient at each interface, and are related to the size and sign of the corresponding index step.

In the example of FIG. 2B, the reflections resulting from the front and back plastic covers of the floppy disk, represented by distorted replicas 207 and 211, are clearly resolved. However, the thickness of the magnetic recording material is so small that the waveforms returned from its front and back surfaces cannot be distinguished, and appear as a single distorted replica 209. The incident waveform 201 hardly changes its shape while traversing test object 107 because the plastic material of the floppy disk has little absorption and little dispersion. If other types of test objects are used, the reflected waveforms may be significantly altered in shape.

FIG. 2C shows a waveform 215 that represents waveform 205 to which various numerical processing steps have been applied. These steps include a filtered Fourier deconvolution of the terahertz detector 105 (FIG. 1) instrument response, followed by a wavelet filtering process to remove noise. This numerical processing produces a sharp spike at each time delay that corresponds to the position of a reflecting interface. Thus, numerical processing helps to more accurately determine the positions of the various interfaces. In contrast to waveform 205 of FIG. 2B, the front and back surfaces of the thin (~120 mm) magnetic recording material are clearly observed in the processed waveform 215 of FIG. 2C. This is consistent with the expected resolution of $L_c/2$, where $L_c$=200 microns is the coherence length of the THz pulse in the intervening material. In contrast, when no other reflections are nearby, the position of a reflecting surface can be determined with a precision of only a few microns. Note that the amplitude of waveform 205 (FIG. 2B) has been scaled up by a factor of four, and that the three curves have been vertically offset along the amplitude axis for clarity. In FIG. 2D, the refractive index profile of the object has been extracted from the processed waveform of FIG. 2C according to the procedure disclosed below in connection with equation (3).

Figure 3A:
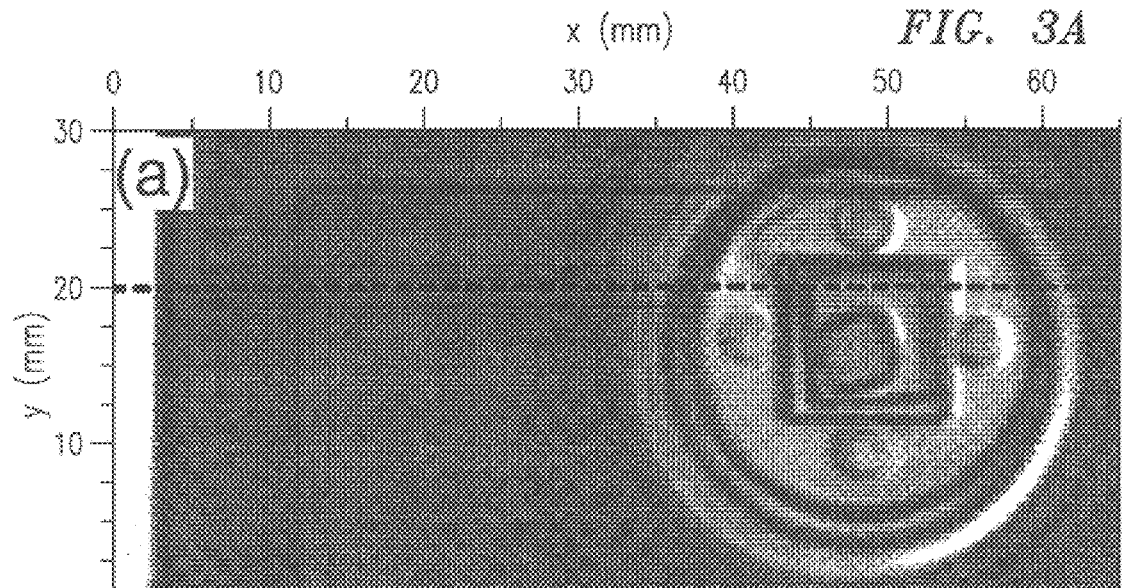
FIG. 3A shows a prior art tomographic ray image.
Figure 3B:
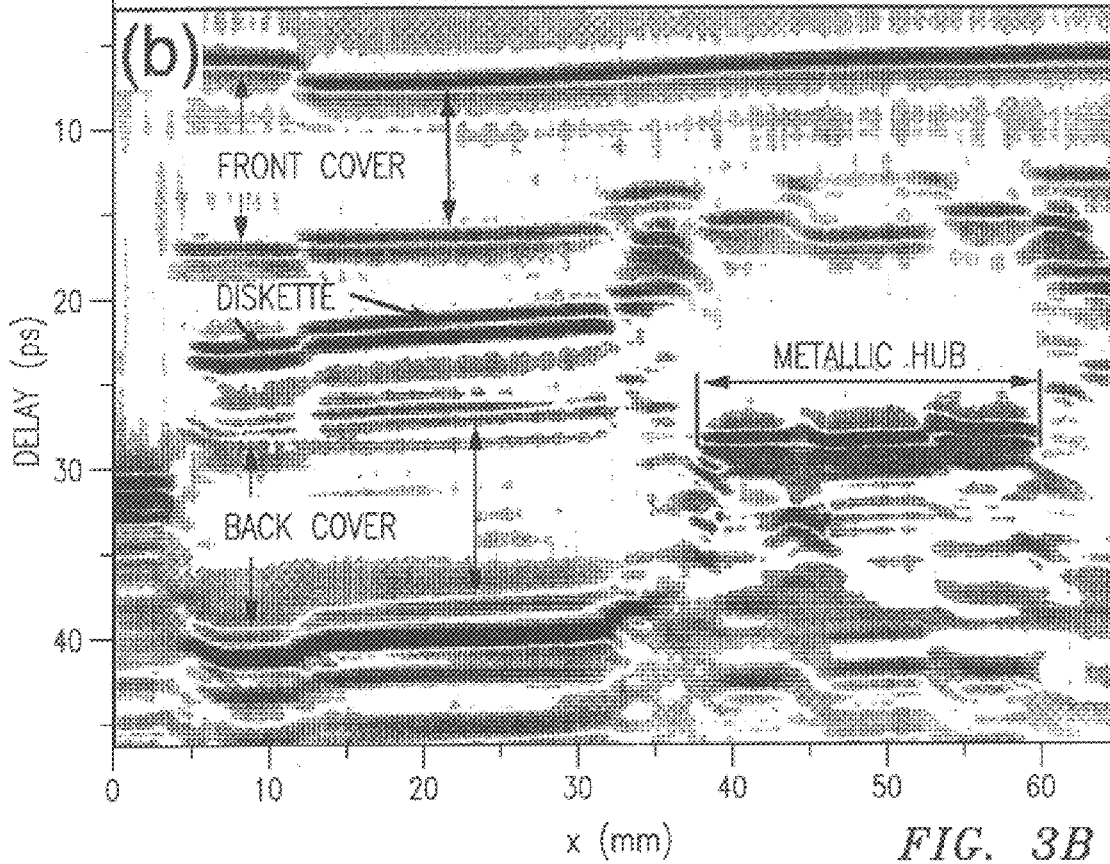
FIG. 3B shows a depth-resolved slice of a test object using the imaging techniques disclosed herein.

FIGS. 3A and 3B are images of a test object obtained using the system to of FIG. 1. The test object is a floppy disk, and the image of FIG. 3A represents a prior-art two-dimensional image of the disk obtained by measuring reflections of terahertz pulses by the disk. More specifically, the image of FIG. 3A was obtained by computing the total reflected power using real-time processing of the reflected waveforms with a digital signal processing device (DSP), with the reflected power translated into a gray scale. This is roughly similar to the original T-ray imaging introduced in U.S. Pat. No. 5,623,145, but note that reflection geometry is used in the present invention. The plastic cover of the floppy disk with its various features, the circular recording disk within the floppy, as well as the metallic hub in the center of the disk can be clearly identified in the image of FIG. 3A.

In FIG. 3B, a tomographic T-ray "slice" of the floppy disk is shown at a particular vertical position (y=20 mm), indicated by the dashed line in FIG. 3A. The field amplitude of the reflected T-Ray waveforms for each horizontal (x) position is displayed as a function of delay in this tomographic image. The absolute amplitude of the reflected waveforms is translated into a gray scale, so that each single-cycle "distorted replica" of the input wave appears as a double dark stripe (refer to FIG. 2B, 207, 209, 211). The vertical axis of FIG. 3B (delay) is related to depth within the floppy disk in the direction of propagation of the incident terahertz pulse beam. The positions of the various parts of the floppy disk along the propagation direction of the THz beam can be observed clearly in this tomographic picture, such as the front and back cover, the magnetic recording disk, and the metallic hub of the disk (as indicated). The picture also shows some artifacts of the technique resulting from multiple reflections between the various interfaces, such as the features observed behind the substantially opaque hub of the disk.

Terahertz waveforms reflected by test objects may be subjected to signal processing steps in order to more readily ascertain the structure of layers within the test object at any given (x,y) position on the test object. The reflected waveform B(t), an example of which is given in FIG. 2B, is mathematically related to the incident waveform A(t) (FIG. 2A). The relationship between A(t) and B(t) may be determined by convoluting the impulse response g(t) of the layered medium:

$$B_j = \sum_{k=0}^{M} g_{j-k} A_k. \quad (1)$$

In the above expression, discrete-time functions are employed. Each of these discrete-time functions is defined by digitization with a time step $\Delta t$ (e.g., $B_k=B(k\times\Delta t)$). M is the number of samples in the digitized waveforms, and 1024 is used in the present example. The impulse response g(t) is characteristic of the test object itself and does not depend upon the details of the incident terahertz pulse. The coefficient $g_k$ is the amplitude of the radiation returning from the object in the $k^{th}$ time slot. It is determined by the reflection off of the $k^{th}$ layer as well as by transmission through the preceding layers, $j=1,\ldots,k-1$, once in each direction along the propagation path of the terahertz beam.

The distance $d_j$ between two adjacent layers j and j+1 of a test object is related to the time separation of the two corresponding reflections $\Delta t = t_{j+1} - t_j$ by:

$$d_j = \frac{c}{2\times n_j} \times Dt, \quad (2)$$

where $n_j$ is the refractive index of the medium between surfaces j and j+1. Therefore, the temporal position of each reflected pulse is related to the position of the reflecting interface in the test object along the direction of propagation of the incident terahertz beam.

An approximation for the impulse response function g(t) is obtained by mathematically deconvoluting the measured waveforms A(t) and B(t). Given g(t), the refractive index profile of the layered structure can then be reconstructed. In discretized form, the $j^{th}$ time step corresponds to a layer of thickness $d_j$ given by equation (2), and of refractive index $n_j$ given by:

$$n_j = \prod_{i=1}^{j} \frac{1-r_i}{1+r_i}, \quad (3)$$

where the reflection coefficients $r_k$ are defined iteratively in terms of $g_k$ and the previous reflections, by the relation:

$$r_k = g_k \cdot \prod_{j=1}^{k-1} \frac{1}{(1-r_j^2)}. \quad (4)$$

Here $r_1=g_1$, and, by definition, the initial reference plane has $n_0=1$. These expressions are valid in the context of small reflection coefficients, when multiple reflections are negligible. Also, note that absorption and dispersion effects are neglected.

A full three-dimensional representation of the object can be constructed just as rapidly as a two-dimensional image, because all of the information about the third dimension (the depth) is contained in a single waveform (i.e., the waveform of FIG. 2B and/or FIG. 2C). For example, the tomographic image in FIG. 3B consists of 217 waveforms and took roughly 10 seconds to acquire, with each waveform recorded in 50 ms.

Although tomographic T-ray imaging may be applied to various operational environments in which ultrasonic imaging has been used, a commonly encountered problem in ultrasonic imaging is the large difference in acoustic impedance between air and liquid or solid objects, which necessitates some form of index matching. For terahertz waves, the dielectric constants of many dielectrics are not too different from that of air, and index matching is not required for T-ray tomography. Many materials such as plastic, cardboard, wood and rubber have good transparency in the terahertz frequency range. Hence, the techniques disclosed herein can be effectively used in many quality control applications, for example to detect voids or cracks. Another application area for T-ray tomography is burn diagnostics. While the strong water absorption precludes the use of THz radiation in biomedical research inside the body, it may be possible to obtain quantitative and highly sensitive measurements of burn depth and burned tissue properties using THz tomography in dermatological medicine.

In conclusion, disclosed herein are improved terahertz imaging techniques that operate in a reflection geometry. In the reflection geometry, timing information is correlated to depth information, and tomographic slices of objects can be obtained to provide 3-dimensional T-ray tomography on a wide range of test objects. In T-ray tomographic imaging, one can isolate successive reflections in the time domain, and extract information about each layer of a layered test object individually. In this fashion, detailed spectroscopic information can be obtained about sub-surface layers, with the potential for material identification. The range of potential applications for T-ray tomography is extremely broad, encompassing such wide-ranging fields as biomedical imaging, package inspection, and quality control.

We claim:

1. A method of providing a compositional image of an object in real time including the steps of:
    (a) illuminating the object with a waveform comprising pulses of electromagnetic radiation in the terahertz frequency range, and
    (b) measuring the relative time delays of pulses reflected by the object to determine the positions of discontinuities in the object.

2. The method of claim 1 wherein the pulses of electromagnetic radiation include one or more pulses having a duration in the range of approximately 10 to 10,000 femtoseconds.

3. The method of claim 1 wherein the discontinuities are dielectric interfaces.

4. The method of claim 3 wherein the step of measuring further includes the step of using the relative time delays to provide a full-volume image of the object in real time, wherein the full-volume image is defined as an image that shows the locations of compositional discontinuities within the volume of the object.

5. A method of providing a compositional image of an object in real time including the steps of:
    (a) illuminating the object with a waveform comprising pulses of electromagnetic radiation in the terahertz frequency range, the object reflecting at least a portion of the electromagnetic radiation as reflected pulses, the electromagnetic radiation traveling substantially along a direction of propagation defined by a set of parallel axes,
    (b) receiving the reflected pulses at a detector,
    (c) measuring the arrival times of each of a plurality of reflected pulses as received at the detector; and
    (d) from the arrival times, determining the location of dielectric interfaces in the object along the direction of propagation.

6. The method of claim 5 wherein the pulses of electromagnetic radiation include one or more pulses having a duration in the range of approximately 10 to 10,000 femtoseconds.

7. The method of claim 6 wherein the pulses of electromagnetic radiation include a first pulse separated in time from a second pulse, and the step of measuring further comprises the step of determining elapsed time between receipt of the first pulse as reflected by the object and receipt of the second pulse as reflected by the object.

8. The method of claim 7 wherein the step of measuring further includes the step of using the elapsed time to provide a full-volume image of the object in real time, wherein the full-volume image is defined as an image that shows the locations of compositional discontinuities within the volume of the object.

9. The method of claim 5 wherein the pulses reflected by the object are analyzed in the time domain to provide a 3-dimensional tomographic image of the object.

10. The method of claim 5 wherein the analysis of the reflected waveform uses the arrival times of reflected pulses to determine the location of dielectric interfaces along the direction of propagation of the terahertz radiation.

11. An apparatus for providing a compositional image of an object in real time including:
 (a) a source of electromagnetic energy for illuminating the object with pulses of radiation in the terahertz frequency range, and
 (b) a measuring device for determining the positions of discontinuities in the object by measuring the relative time delays of pulses reflected by the object.

12. The apparatus of claim 11 wherein the source of electromagnetic energy produces pulses each having a duration in the range of approximately 10 to 10,000 femtoseconds.

13. The apparatus of claim 11 wherein the object includes discontinuities in the form of dielectric interfaces.

14. The apparatus of claim 11 further including an imaging device coupled to the measuring device for using the relative time delays to provide a full-volume image of the object in real time, the full-volume image including compositional information about the object.

15. An apparatus for providing a compositional image of an object in real time including:
 (a) a source of electromagnetic energy for illuminating the object with pulses of electromagnetic radiation in the terahertz frequency range, the object reflecting at least a portion of the electromagnetic radiation as reflected pulses, the electromagnetic radiation traveling substantially along a direction of propagation defined by a set of parallel axes,
 (b) a detector for receiving the reflected pulses,
 (c) a measuring device coupled to the detector for measuring the arrival times of each of a plurality of reflected pulses as received at the detector; and
 (d) a calculating device for determining, from the arrival times, the location of dielectric interfaces in the object along the direction of propagation.

16. The apparatus of claim 15 wherein the pulses of electromagnetic radiation include one or more pulses having a duration in the range of approximately 10 to 10,000 femtoseconds.

17. The apparatus of claim 16 wherein the pulses of electromagnetic radiation include a first pulse separated in time from a second pulse, and the measuring device further comprises a device for determining elapsed time between receipt of the first pulse as reflected by the object and receipt of the second pulse as reflected by the object.

18. The apparatus of claim 17 further including an imaging device, coupled to the measuring device, adapted for using the elapsed time to provide a full-volume image of the object in real time, wherein the full-volume image is defined as an image that shows the locations of compositional discontinuities within the volume of the object.

19. The apparatus of claim 18 wherein the object comprises a gas or a gas mixture, and the imaging device is adapted to generate an image of the gas or gas mixture using linear predictive coding.

20. The apparatus of claim 19 wherein the measuring device analyzes pulses reflected by the object in the time domain, so as to permit the imaging device to provide a 3-dimensional tomographic image of the object.

21. The apparatus of claim 15 wherein the analysis of the reflected waveform uses the arrival times of reflected pulses to determine the location of dielectric interfaces along the direction of propagation of the terahertz radiation.

22. A method of providing an image of an object in real time including the steps of:
 (a) illuminating the object with a waveform comprising pulses of electromagnetic radiation in the terahertz frequency range, the object reflecting at least a portion of the electromagnetic radiation as reflected pulses, the electromagnetic radiation traveling substantially along a direction of propagation defined by a set of parallel axes,
 (b) receiving the reflected pulses at a detector,
 (c) measuring the arrival times of each of a plurality of reflected pulses as received at the detector;
 (d) signal processing and filtering the plurality of reflected pulses to obtain an approximation of an impulse response function for the object;
 (e) converting the measured arrival times into depth information for the object; and
 (f) obtaining one or more materials properties of the object from the impulse response function for the object.

23. The method of claim 22 wherein the signal processing step includes deconvolving the reflected pulses with a reference waveform.

24. The method of claim 22 wherein the filtering step includes a wavelet filtering process for removing noise accumulated in the deconvolution process.

25. The method of claim 22 wherein the materials properties include a refractive index profile for the object.

26. The method of claim 25 wherein information about the refractive index profile of the object is determined from the magnitude of the reflection coefficient of each dielectric discontinuity.

27. The method of claim 22 further including the step of calculating signal attenuation of reflected pulses due to one or more reflections and/or absorptions from compositional layers situated between the illuminating electromagnetic radiation and a specified discontinuity in the object.

* * * * *